United States Patent [19]

Thomas et al.

[11] 3,950,322

[45] Apr. 13, 1976

[54] FLUOROGENIC SUBSTRATE GLYCOSIDES

[75] Inventors: John J. Thomas, Satellite Beach; Edward C. Folger, Melbourne, both of Fla.

[73] Assignee: Research Corporation, New York, N.Y.

[22] Filed: Aug. 27, 1973

[21] Appl. No.: 391,702

[52] U.S. Cl.... 260/210 R; 195/103.5 R; 260/211 R; 260/234 R; 424/180
[51] Int. Cl.² .......................................... C07H 17/06
[58] Field of Search ..................... 260/210 R, 211 R

[56] References Cited
UNITED STATES PATENTS

| | | | |
|---|---|---|---|
| 3,152,115 | 10/1964 | Morel et al. | 260/211 R |
| 3,427,300 | 2/1969 | Sarette et al. | 260/211 R |
| 3,445,455 | 5/1969 | Kiss et al. | 260/210 R |
| 3,755,118 | 8/1973 | Partridge et al. | 260/210 R |
| 3,758,455 | 9/1973 | Arita | 260/210 R |

*Primary Examiner*—Johnnie R. Brown
*Attorney, Agent, or Firm*—Behr & Woodbridge

[57]. ABSTRACT

There are provided novel fluorogenic substrates comprising a ketoside formed between an N-acyl neuraminic acid and a highly fluorescent material containing a phenolic grouping. The presence of neuraminidase is detected by contacting the aforementioned fluorogenic substrate with a sample suspected of containing neuraminidase. Neuraminidase, if present, cleaves the ketosidic linkage, releasing the fluorescent material which is then detected by known methods. There is also provided a novel and efficient method of preparing such fluorogenic substrates utilizing cadmium carbonate as a catalyst.

15 Claims, 2 Drawing Figures

FLUOROGENIC SUBSTRATE GLYCOSIDES

FIELD OF THE INVENTION

Fluorogenic detection of the enzyme neuraminadase.

BACKGROUND OF THE INVENTION

It is known that the enzyme neuraminidase is associated with the RNA viri of the myxovirus group which contains many highly infectious and pathogenic subgroups such as rubella, influenza, rabies, etc. The detection of the presence of this enzyme as an indicator of the presence of viri of the myxovirus group has been the subject of much work in recent years. It is well known that neuraminidase (hereinafter NASE) will cleave a ketosidic linkage between neuraminic acid as well as certain simple derivatives thereof and compounds which originally contained a phenolic or an alcoholic group, the oxygen atom of the phenolic or alcoholic group forming the ethereal oxygen of the ketosidic linkage. Methods were therefore devised to provide such ketosides and to detect the presence of NASE by testing the reaction mixture of the suspected sample and the ketosidic substrate for the presence of the phenol containing moiety. Several approaches to this problem have been developed. Most of them however depend upon the detection of a chromophoric moiety. Heretofore, the chromophoric moiety has been provided by the reaction of the liberated phenol with other chemical entities. Examples of this are to be found in the method disclosed by Tuppy, et al, for example, in FEBS Letters, 3, 72–75 (1969) and J. Virol., 6 556–558 (1970). An alternative is the chiobarbituric acid assay of sialic acids (J. Biol. Chem. 234, 1971–1975 (1959).

While these chromophoric methods are operative they leave much to be desired in the area of sinsitivity, and efficiency of operation. Conversion of the liberated alcoholic or phenolic moiety to a chromophore makes enzyme kinetic measurements time consuming, tedious, and costly. Thus, in screening work it would be desirable to detect the presence of viri of the myxovirus category quickly before clinical symptoms have appeared. In this, the incubation period of the disease, the virus is present in the system but often in rather small amounts. The presently available methods are not sensitive enough to detect the presence of the viri in the preclinical stages.

It would therefore be desirable to provide a NASE sensitive substrate which, upon reaction with NASE would provide a material detectable at extremely low concentrations since the production of such material is dependent upon the concentration of NASE which in turn is dependent upon the concentration of virus.

It would further be desirable to provide an efficient method of producing such a substrate.

Recent work in this area includes that of Privalova and Khorlin (Izvestiya Akademii Nauk SSR (Chemical Series) 2785 (1969)) in which the ketoside is formed between p-nitrophenol and the methyl ester of 2-chloro, 0- Tetracetyl-N-acetyl neuraminic acid utilizing silver carbonate as a catalyst. The NASE sensitive substrate was prepared by saponification of this acetylated ketoside to remove the 0-acetyl groups.

Conrow and Bernstein (J. Org. Chem., 36, 863 (1971)) found that certain steroids having a phenolic A-ring will readily form a glycosidic linkage with 0-tetraacetyl-2-bromoglucopyranose in the presence of a cadmium carbonate catalyst. It should be noted that the acetyl haloglucopyranose utilized by Conrow has a much simpler structure, especially in the steric sense than neuraminic acid or its derivatives. In particular, it should be noted that Conrow's material is not only devoid of an amino or amido group at the 5 position of the pyranose ring but, more importantly, is totally unsubstituted at the 2 position of the pyranose ring which, in Conrow's compound bears only the halo moiety, whereas in N-acetyl neuraminic acid that position bears a carboxy group which may be further converted into an ester grouping. Consideration of steric models demonstrate therefore that the 2 position of neuraminic acid is highly hindered and difficulties in reaction at that point might be expected.

SUMMARY OF THE INVENTION

The formation of the fluorogenic substrate utilized in the present invention is summarized in the flow diagram below.

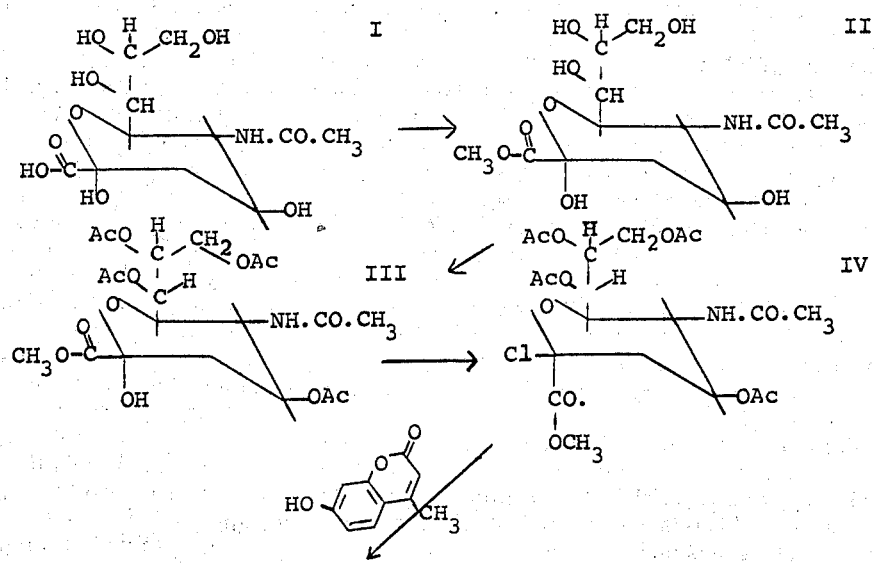

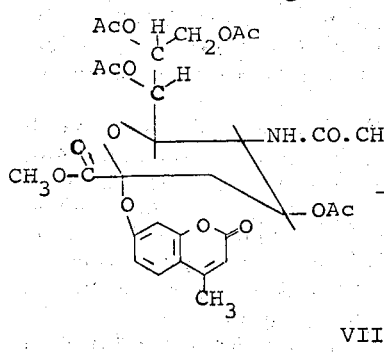

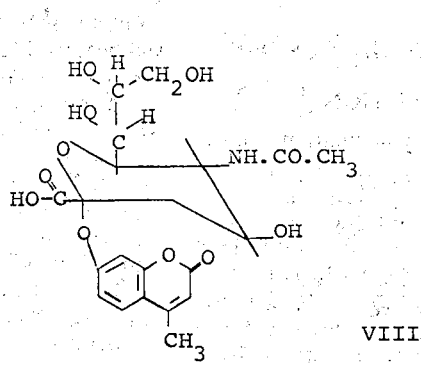

In this procedure an N-acyl neuraminic acid, suitably commercial N-acetyl neuraminic acid (I) is methylated to provide the corresponding methyl N-acetyl neuraminate which is then 0-acylated, suitably acetylated to provide the o-tetraacyl-N-acylneuraminic ester for example the methyl 4,7,8,9-0-tetraacetyl-N-acetyl neuraminate (III) which is then converted into the corresponding 2-halo compound with a suitable halogenating agent preferably a chlorinating agent to form the corresponding 2-chloro compound (IV).

The compound (IV) is then coupled with a highly fluorescent material containing a phenolic moiety (Flu-.OH) to form the resulting ketoside (VII). This ketoside is then partially saponified to remove all 0-acyl groups but leaving the N-acyl group and the ketosidic linkage intact.

The presence of NASE may be detected in a test substance by adding thereto a small amount of the fluorogenic substrate (VIII) and an equal amount to a control sample known to be free of NASE. The test and control samples are allowed to stand for a short period of time and aliquots of each sample are transferred to a fluorometer for detection of fluorescence. An increased reading for the test sample over the control sample indicates the presence of NASE in the tested material.

DESCRIPTION OF THE PREFERRED EMBODIMENTS

Figure 1:
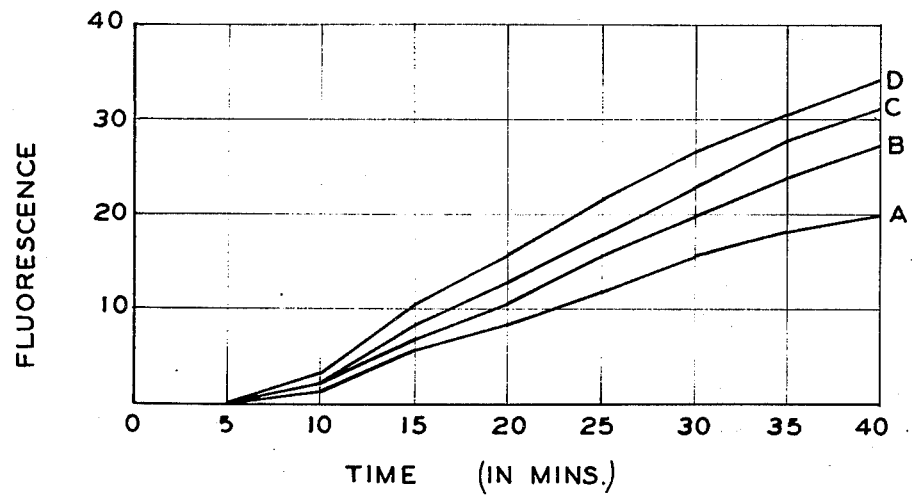

In the process of the present invention the starting material (Compound I) is an N-acylneuraminic acid. There may be used any compound within this category which, after formation of a ketosidic linkage at the 2 position will be regenerated by treatment of the said ketoside with NASE. It is generally preferred to utilize a small acyl moiety preferably a small alkanoyl moiety having 1 to 5 carbon atoms. It is especially preferred to utilize N-acetyl neuraminic acid as a starting material chiefly because this material is readily available commercially. The conversion of Compound (I) to the corresponding 0-tetraacyl ester (III) is carried out by methods well known in the art (the method of Tuppy (Monatsch. Chem. 98, 53 (1967) may be utilized). It should be noted that since these acyl groups are removed prior to the utilization of the ketoside, their nature is not critical, any readily available acylating group may be used which will react with a hydroxyl group on a pyranose ring and be readily removed therefrom without damage to the ring. Thus, lower alkanoyl groups containing 1–5 carbon atoms or phenyl lower alkanoyl groups such as benzoyl may be employed. The Compound (III) is then converted into the corresponding 2-halo compound such as the 2-chloro, the 2-bromo, or the 2-iodo compound. It is generally preferred however to prepare the 2-chloro compound. In the preferred procedure Compound (III) is taken up in cooled acetyl chloride, preferably at dry ice/acetone temperatures, anhydrous hydrogen chloride passed into the reaction mixture suitably for about 1 hour at the same temperature, and the entire mixture sealed, suitably in a dry prechilled Carius tube, and maintained at ambient temperature for between 10 and 24 hours. It is desirable to retreat any given batch of material in this manner between 2 and 5 times, suitably about 3 times to obtain maximum reaction. (See also Kuhn, et al., Chem.Ber., 99, 611 (1966)). The thus obtained Compound (VI) is then coupled with a fluorescent material to yield the immediate precursor of the fluorogenic substrate. While it is important for the purposes of the present invention that the fluorescent material shall be highly fluorescent and contain a phenolic moiety therein, the invention is in no way limited to any particular fluorescent material although certain fluorescent materials will be named hereinbelow as suitable and one particular one as especially suitable.

As stated heretofore the only criterion for the fluorescent substance, other than its ability to form a ketosidic linkage, is that it shall be highly fluorescent. It is generally recognized in the art what is meant by this term. While in no way limiting the invention thereto, it is desirable to utilize materials which have an excitation wave length and emission wave lengths in the optically visible range of the spectrum, i.e. ca. 350–650 nm and are detectable at their emission peaks at a fluorescence factor (pF) of at least 2.

For the purposes of this discussion the term fluorescence factor (or pF) is designated as $\log_{10} 1/[c]$ where $[c]$ is the detectable concentration, (as measured on a Turner Model 110 Fluorometer, G. K. Turner Associates, 2524 Pulgas Avenue, Palo Alto, Calif. 94303) in $\mu g/ml$. Thus, where $10^{-3}$ $\mu g/ml$. are detectable the fluorescence factor would be 3. The term detectable is further defined as a peak having a signal/noise ratio on said instrument of at least 10:1.

The fluorescent material must be excited and emit in the visible range so as to avoid false readings from NASE which fluoresces in the U.V. range. Especially preferred for use in the present invention are fluorescein, methylfluorescein, umbelliferone, methylumbelliferone, resorufin, and derivatives thereof having a sufficiently high fluorescence factor as well as at least one phenolic group. It has been found that especially good results are obtained utilizing methylumbelliferone as the fluorescent material.

In the process of preparing the immediate precursor of the fluorogenic substrate the reaction is carried out in the presence of cadmium carbonate in a suitable reaction inert organic solvent. It is desirable that the solvent shall be capable of forming a reasonably efficient azeotrope with water and it is especially desirable for the solvent to have a boiling point of between 100° and 200°C. If the reaction is carried out below this range, then reaction times become inconveniently long, whereas above this temperature range, losses from degradation of the organic components, especially the sugar components are likely to occur. Thus, it has been found that toluene, xylene, and mesitylene are suitable. Toluene has been found to be especially suitable. In carrying out the process a suspension of the fluorescent material and a substantially equimolar amount of cadmium carbonate in the solvent is prepared. While the invention is in no way limited to the use of equimolar amounts, it has been found that superior results are obtained in this fashion. The reaction mixture is heated to reflux in such a manner that the solvent is continually removed but at the same time is replaced with fresh anhydrous solvent. In the preferred modification of the procedure, the distillation continues until the amount of solvent added is substantially equal to the amount of solvent originally present. To this suspension is added the previously prepared compound (III), suitably in chloroform solution. Distillation is then slowly continued until the volume of solvent is reduced to approximately 10% of its original volume. The reaction mixture is then taken up in a suitable solvent and worked up in the usual manner to yield the ketoside (VII). The fluorogenic substrate (VIII) is then prepared by subjecting the ketoside (VII) to selective saponification which will remove the 0-acyl groups as well as the alkyl moiety and the 2-carboxyl group while leaving the N-acyl moiety and the ketoside linkages intact. It has been found that a suitable method of saponification is utilizing alkali metal alkoxide in alkanol, for example, sodium methoxide in methanol may be carried out at temperatures from between ambient (i.e. circa 20°C) down to 0°C. It has been found that a cleaner product is obtained by reaction at around 5°C using 0.1N sodium methoxide in methanol for from about 2 to about 5 hours. Thereafter, a small amount of aqueous alkali, for example, 1N sodium hydroxide, is added dropwise over a substantial period, for example, 5 to 12 hours being suitable, and the reaction mixture allowed to remain at ambient temperature for approximately another 12 to 24 hours. The reaction mixture is then brought substantially to neutrality by means of an ion exchange resin, filtered, the filtrate diluted with alkanol, and evaporated to dryness under reduced pressure below 50°C, circa 25° to 40°C being especially preferred. The thus obtained material contains, as is to be expected, an inorganic residue, however, chromatography on silica gel shows only a single spot.

Test runs using standardized neuraminidase have been carried out. Aqueous solutions containing the fluorogenic substrate (VIII) and standardized solutions of neuraminidase have been contacted at pH 7.2. It has been found that hydrolysis of the ketosidic linkage is essentially complete in about 15 minutes. Under these circumstances it has been found that approximately 1 microgram of substrate/ml. of solution will detect a concentration of circa $5.6 \times 10^{-5}$ micrograms/ml. of Clostridium Perfringens neuraminidase in 15 minutes.

FIG. 1 shows the results obtained in a sample test (details given below) wherein a fluorogenic substrate of the present invention was added to a blank control, trypsin, leucine aminopeptidase and NASE, and the fluorescence measured over a period of 40 minutes. The first 3 samples showed no change in a low level of fluorescence while the sample containing the NASE showed a signal: signal ratio (relative to blank) of ca. 4:1 rising to 8:1 at the end of the test time.

Tests were also carried out on various influenza virus samples which indicated not only the presence of NASE therein but the feasibility of utilizing the substrates and procedures of the present invention for their detection.

EXPERIMENTAL 4,7,8,9-tetra-O-acetyl-N-acetyl-$\alpha$-D-neuraminic acid methyl ester (III) was prepared in accordance with the method of Tuppy, et al (Monatsch. Chem. 98, 53, (1967)).

EXAMPLE I

2-Chloro-4,7,8,9-tetra-o-acetyl-N-acetyl-$\alpha$-D-neuraminic acid methyl ester (IV)

A solution of 321.8 mg. of (III) in 10 ml. of acetyl chloride was chilled in a dry ice/acetone bath. The solution is treated with anhydrous hydrochloric acid for 1 hour. After treatment the solution was transferred to a dry, prechilled Carius tube. The tube is sealed and kept 16 hours at room temperature. The tube is opened and the contents are dissolved in 100 ml. chloroform, then carefully evaporated at 35°C under reduced pressure. This treatment is repeated 3 times. The residue, 2-chloro-4,7,8,9-tetra-O-acetyl-N-acetyl-$\alpha$-D-neuraminic acid methyl ester (IV), is dissolved in 25 ml. chloroform and held for use in the next step.

EXAMPLE II

2-O-4-Methylumbelliferyl-4,7,8,9-tetra-O-acetyl-N-acetyl-$\alpha$-D-neuraminic acid methyl ester (VII)

A suspension of 1.0 gm. 4-methyl umbelliferone (V) and 0.5 gm. cadmium carbonate in 200 ml. toluene is prepared. The suspension is heated to distill off the toluene while fresh toluene is added at an equal rate. After 200 ml. has been distilled, the chloroform solution from the previous step (Example I) is added. The white toluene suspension turns pink. The distillation is continued for 2 hours. The reaction mixture is concentrated to 50 ml., cooled, and 200 ml. chloroform added. The insolubles are filtered off and washed with 100 ml. chloroform. The filtrates and wash are combined and evaporated at 35°C under reduced pressure. The residue is dissolved in 10 ml. chloroform and filtered. The insolubles are washed with 10 ml. chloroform. The chloroform solutions are combined and passed through a 22 × 150 mm alumina column using chloroform. The initial 400 mls. of eluate are collected and evaporated to dryness at 35°C at reduced pressure to yield 2-O-4-methylumbelliferyl-4-7,8,9-tetra-O-acetyl-N-acetyl-$\alpha$-D-neuraminic acid methyl ester (VII). Wt. 327.9 mg., yield 74%, M.P. 42°–48°C. Calc. C, 54.04; H, 6.25; N, 2.47; $C_{30}H_{35}N_1O_{15}$-$H_2O$ (667.6) Found: C, 54.13; H, 5.58; N, 2.10

In accordance with the foregoing procedure, but where, in place of 4-methyl umbelliferone, there is utilized: fluorescein, methylfluorescein, resorufin and umbelliferone, there is obtained the corresponding ketosides.

Purity Test

The product is chromatographed on a silica gel thin layer plate (250 $\mu$) using pH 7.4 n-Butanol saturated with water as the developing solution. The pH is adjusted with ammonium hydroxide. The developed plate is viewed under U.V. light and no 4-methylumbelliferone fluorescence is noted. After treating with sulfuric acid, one spot appeared at Rf 0.60 which did fluoresce under U.V. light in a manner similar to 4-methylumbelliferone. This phenomena can be explained as typical of the expected behavour of fluorogenic ketosides. Since ketosides are known to hydrolyze and yield the parent carbohydrate and alcohol (phenol) under acid conditions.

The fluorescent spot could not have resulted from the presence of pure 4-methylumbelliferone since this material has an Rf of 0.90.

EXAMPLE III

2-O-4-methylumbelliferyl-N-acetyl-α-D-neuraminic acid (VIII)

A solution of 0.375 gm. of 2-O-4-methylumbelliferyl-4-7-8,9-tetra-o-acetyl-N-acetyl-α-D-neuraminic acid methyl ester (VII) in 4 ml. methanol is prepared and chilled at 40°C. 0.86 ml. of 0.1N sodium methoxide in methanol is added and the whole is mixed 3 hours at 4°C. After 3 hours, the cooling bath is removed and 1.0N sodium hydroxide is added dropwise over 10–24 hours at room temperature until the pH stabilezes at 9.0. The solution is kept 16 hrs., adjusted to pH 7.2 with amberlite 1R-120, (H+) and filtered. The filtrate is diluted and evaporated to dryness at 35°C under reduced pressure with 150 ml. of methanol to yield 2-O-4-methylumbelliferyl-N-acetyl-α-D-neuraminic acid (VIII). Wt. 314.9 mg, M.P. +200°C with slow decomposition. Theo. $C_{21}H_{23}O_{11}N_1 6H_2O$ 15.5% Inorganic Residue C, 38.01; H, 5.46; N, 2.10 Found: C, 38.37; H, 5.22; N, 2.29 Inorganic Residue 15.5%

The material is chromatographed on a thin layer silica gel (250 μ) plate with n-Butanol saturated with water and 1 drop of concentrated aqueous ammonia. One spot is obtained Rf=0.045. This spot fluoresced as 4-methylumbelliferone upon developing with sulfuric acid. This phenomenon again indicates that the product is a 4-methylumbelliferone ketoside of neuraminic acid since as mentioned before pure 4-metylumbelliferone has an Rf value of 0.90.

In accordance with the foregoing procedures, but where, in place of 2-O-4-methylumbelliferyl-4,7,8,9-tetra-O-acetyl-N-acetyl-α-D-neuraminic acid methyl ester (VII), there is used the corresponding 2-O-fluoresceinyl, methylfluoroesceinyl, -umbelliferyl, and -resorufinyl ketosides produced in accordance with Example II, there are obtained the corresponding 2-O-substituted-N-acetyl-α-D-neuraminic acids.

Detection of Neuraminidase

Measurements were carried out using a Turner Model No. 110 Fluorometer (G. K. Turner Associates, 2524 Pulgas Avenue, Palo Alto, Calif. 94303) utilizing Lamp No. 110–850, cuvettes No. 110–800 (Pyrex.)

| Example A: | Temp. 37°C |
|---|---|
| Filters Primary | 7–60 |
| Filters Secondary | 2A,48 |
| Neutral Density | 10% |
| Attenuation | 3X |
| Reference Solution | pH 7.2 Tris |

Fluorogenic substrate: 2-O-4-methylumbelliferyl-N-acetyl-α-D-neuraminic acid. NASE source: Clostridium perfringens (Sigma Chemical Company, -D-neuraminic No. 698-80901.) Lamp: 110–850

The test was run at 37°C using an enzyme concentration of 149 μg/ml. and fluorogenic substrate concentrations of 8.1, 16.2, 24.3, 32.4, and 40.5 μg/ml. respectively, all in pH 7.2 Tris buffer solutions of neuraminidase. The increase in fluorescence of each solution was plotted versus time and compared with the increase in fluorescence of enzyme and substrate solution blanks. The increase in fluorescence was recorded. (See FIG. 1). The length of time required for complete enzymatic hydrolysis was between 13 and 15 minutes. There was no increase in fluorescence observed with the blanks.

The results are shown in FIG. 1.

| Example B: | Temp. 37°C |
|---|---|
| Filters Primary | 7–60 |
| Filters Secondary | 2A,48 |
| Neutral Density | 10% |
| Attenuation | 1X |
| Reference Solution | pH 7.2 Tris |

Fluorogenic substrate: 2-o-4-methylumbelliferyl-N-acetyl-α-D-neuraminic acid.

Figure 2:
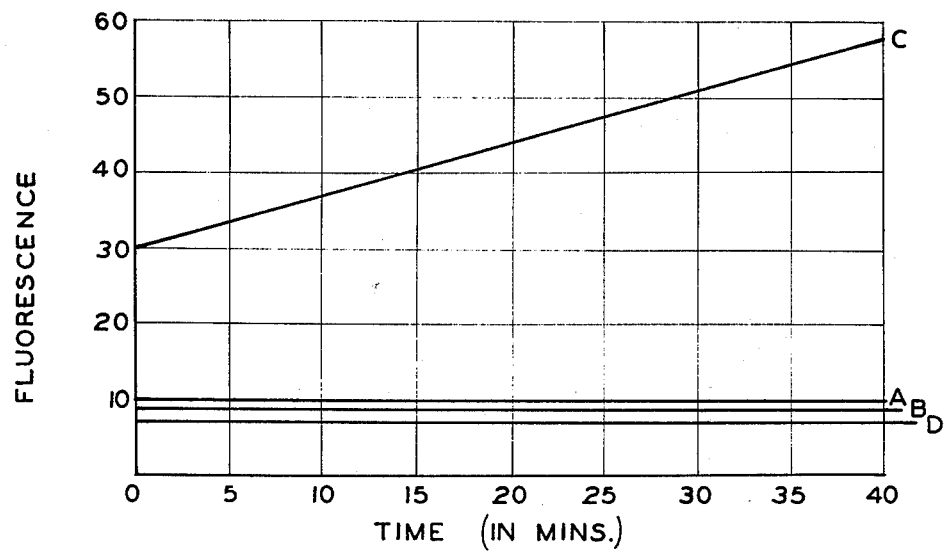

The test was run at 37°C using Trypsin (Difco) at 114.4 μg/ml. (Curve A), Leucineaminopeptidase (Sigma, lot No. 1098-8140), activity: 17.6 μ moles/min. (Curve B), NASE source: Clostridium perfringens (Sigma Chemical Company, lot No. 698-80901, using bovine submaxilliary mucin, $1.16 \times 10^{-4}$ unit, **6.4.5 μg/ml. (Curve C) and blank substrate (Curve D). The results are shown in FIG. 2.

We claim:

1. 2,0-Flu-(N acetyl-neuraminic acid) wherein Flu is an aryl moiety whose origin HO.Flu is selected from the group consisting of fluoroescein, methylfluoroscein, methylumbelliferone, umbelliferone and resorufine.

2. 2-O-4-methylumbelliferyl-N-acetyl-α-D-neuraminic acid being a compound of claim 1.

3. 2-0-fluoresceinyl-N-acetyl-α-D-neuraminic acid being a compound of claim 1.

4. 2-0-umbelliferyl-N-acetyl-α-D-neuraminic acid being a compound of claim 1.

5. 2-0-methylfluoresceinyl-N-acetyl-α-D-neuraminic acid being a compound of claim 1.

6. 2-0-resorufinyl-N-acetyl-α-D-neuraminic acid being a compound of claim 1.

7. In the process of preparing a compound of claim 1 the process comprising:
   refluxing a 2-halo-4,7,8,9-tetra-0-acyl-N-acyl neuraminic acid ester with HO.Flu in a reaction inert organic solvent capable of forming a solvent/water azeotrope in the presence of cadmium carbonate wherein acyl is alkanoyl of 1–5 carbon atoms or phenyl alkanoyl of 1–5 carbon atoms in the alkoxyl moiety, and halo is chloro, bromo or iodo.

8. The process of claim 7 wherein the reaction is carried out in a reaction inert organic solvent of b.p. 80°–200°C.

9. The process of claim 8 wherein the solvent is toluene or xylene, or mesitylene.

10. The process of claim 7 wherein acyl is acetyl, and the ester is a methyl ester.

11. The process of claim 10 wherein the solvent is toluene or xylene, or mesitylene.

12. A process of preparing 2-0-Flu-(N-acetyl-neuraminic acid) comprising:
   a. the process of claim 7,
   b. saponification of the 0-acyl moiety and the ester moiety.

13. A process of claim 12 wherein saponification is carried out by reaction with an alkali metal alkoxide.

14. A process of preparing 2-0-Flu-(N-acetyl-neuraminic acid) comprising:
 a. the process of claim 10;
 b. saponification of the 0-acetyl moiety and the methyl ester moiety.

15. A process of claim 14 wherein saponification is carried out by reaction with an alkali metal alkoxide.

* * * * *